United States Patent
Lv et al.

(10) Patent No.: US 12,059,345 B2
(45) Date of Patent: Aug. 13, 2024

(54) TRANSCATHETER PROSTHETIC VALVE REPLACEMENT SYSTEM

(71) Applicant: JENSCARE SCIENTIFIC CO., LTD., Zhejiang (CN)

(72) Inventors: Shiwen Lv, Ningbo (CN); Yibin Li, Ningbo (CN); Zhi Chen, Ningbo (CN); Kan Lu, Ningbo (CN)

(73) Assignee: JENSCARE SCIENTIFIC CO., LTD., Zhejiang (CN)

( * ) Notice: Subject to any disclaimer, the term of this patent is extended or adjusted under 35 U.S.C. 154(b) by 684 days.

(21) Appl. No.: 17/299,257

(22) PCT Filed: Nov. 28, 2019

(86) PCT No.: PCT/CN2019/121425
§ 371 (c)(1),
(2) Date: Jun. 2, 2021

(87) PCT Pub. No.: WO2020/114296
PCT Pub. Date: Jun. 11, 2020

(65) Prior Publication Data
US 2022/0039948 A1  Feb. 10, 2022

(30) Foreign Application Priority Data

Dec. 3, 2018 (CN) .......................... 201811462571.1

(51) Int. Cl.
*A61F 2/24* (2006.01)
(52) U.S. Cl.
CPC .......... *A61F 2/2418* (2013.01); *A61F 2/2436* (2013.01); *A61F 2/2457* (2013.01); *A61F 2/2409* (2013.01); *A61F 2/2412* (2013.01)
(58) Field of Classification Search
CPC ..... A61F 2/2418; A61F 2/2457; A61F 2/2436
See application file for complete search history.

(56) References Cited

U.S. PATENT DOCUMENTS

| 8,449,599 | B2 | 5/2013 | Chau et al. |
| 2005/0137695 | A1 | 6/2005 | Salahieh et al. |
| 2015/0173897 | A1* | 6/2015 | Raanani ............... A61F 2/2436 |
| | | | 623/2.11 |

FOREIGN PATENT DOCUMENTS

| CN | 102639179 | 8/2012 |
| CN | 103079498 | 5/2013 |

(Continued)

OTHER PUBLICATIONS

International Search Report issued for International Patent Application No. PCT/CN2019/121425, Date of mailing: Feb. 21, 2020, 12 pages including English translation.

*Primary Examiner* — Suba Ganesan
(74) *Attorney, Agent, or Firm* — HSML P.C.

(57) ABSTRACT

The present application relates to a transcatheter prosthetic valve replacement system including a delivery catheter, a frame, a prosthetic valve, and one or more clamping devices. The prosthetic valve is fixed in the frame. The clamping device is connected to a periphery of the frame. The frame and the clamping device can be preloaded in the delivery catheter. The clamping device includes a clamping member, a collar, and a control member. One end of the clamping member is a fixation end which is fixedly connected to the frame, and the other end of the clamping member is a deployable resilient segment which can be compressed and released. The collar is slidably sleeved on the clamping member. One end of the control member is connected to the collar, and the other end of the control member is manipulated outside the body. From being compressed to being fully released, the clamping member in sequence has two configurations. In the first configuration, the collar is moved along the clamping member towards a free end of the deployable resilient segment, and the deployable resilient segment is gradually closed. In the second configuration, the (Continued)

collar is moved along the deployable resilient segment towards the fixation end, and the deployable resilient segment recovers its predetermined shape.

15 Claims, 8 Drawing Sheets

(56) References Cited

FOREIGN PATENT DOCUMENTS

| | | |
|---|---|---|
| CN | 103997990 | 8/2014 |
| CN | 105682611 | 6/2016 |
| CN | 106264793 | 1/2017 |
| CN | 106456321 | 2/2017 |
| CN | 108348321 | 7/2018 |
| CN | 109350307 | 2/2019 |
| CN | 209661883 U | 11/2019 |
| WO | 2011137531 | 11/2011 |
| WO | 2018005779 | 1/2018 |

* cited by examiner

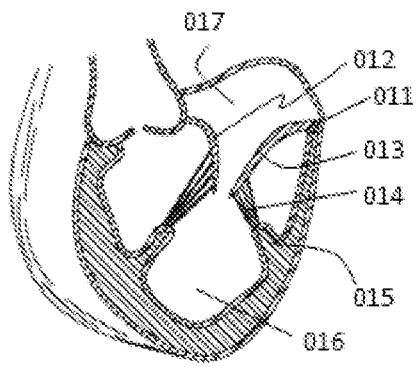
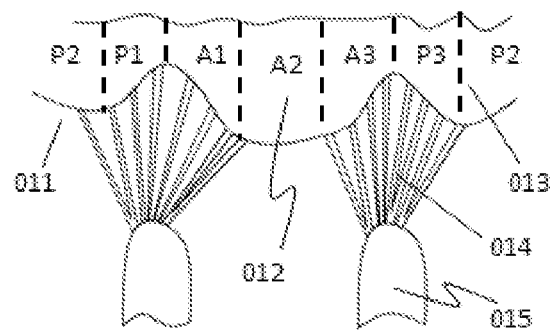
FIG. 1A
FIG. 1B
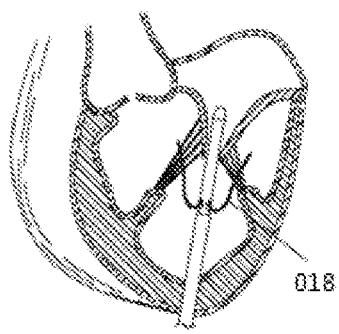
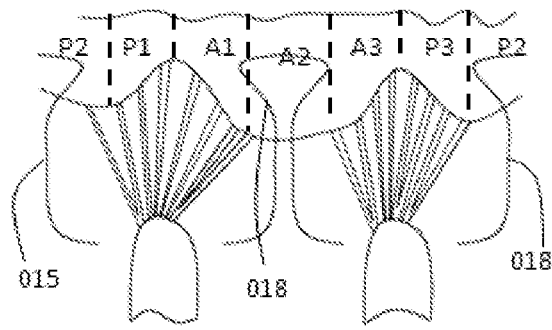
FIG. 1C (Prior Art)
FIG. 1D (Prior Art)
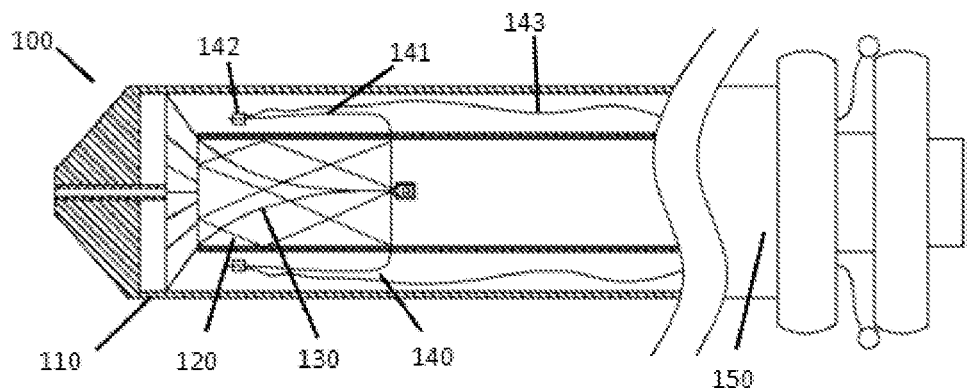
FIG. 2A

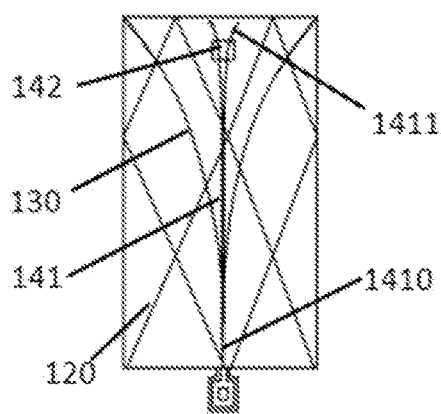
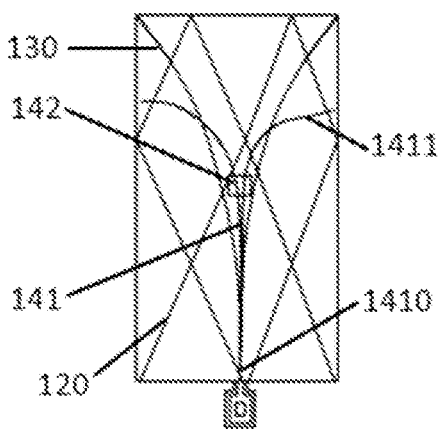
FIG. 2B    FIG. 2C
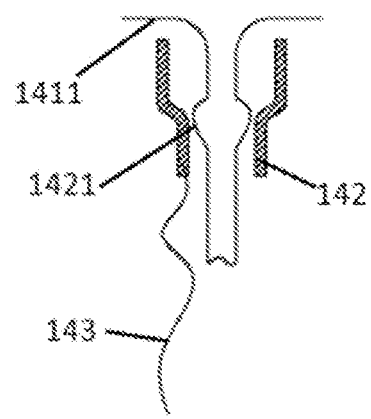
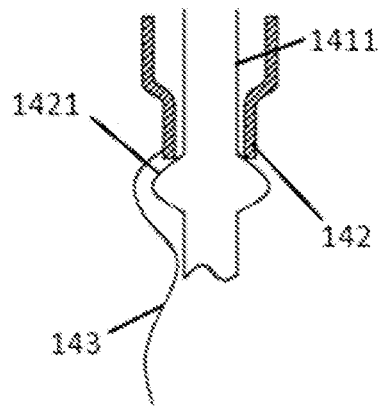
FIG. 3A    FIG. 3B
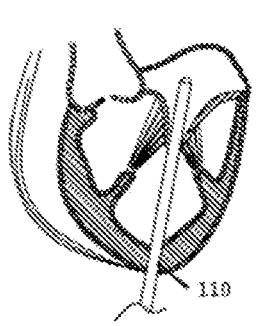
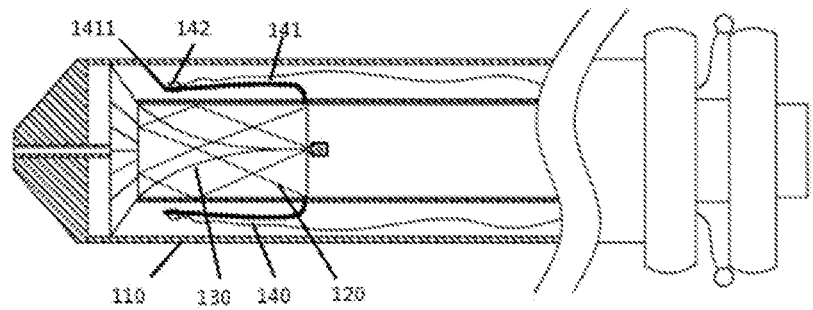
FIG. 4A    FIG. 4B

TRANSCATHETER PROSTHETIC VALVE REPLACEMENT SYSTEM

CROSS-REFERENCE TO RELATED APPLICATION

This application claims priority from Chinese Patent Application No. 201811462571.1, entitled "TRANSCATHETER PROSTHETIC VALVE REPLACEMENT SYSTEM", filed on Dec. 3, 2018, the entirety of which is incorporated by reference herein. This application is a national phase under 35 U.S.C. § 120 of international patent application PCT/CN2019/121425, entitled "TRANSCATHETER PROSTHETIC VALVE REPLACEMENT SYSTEM" filed on Nov. 28, 2019, the content of which is also hereby incorporated by reference.

FIELD

The present application relates to the field of medical apparatus, particularly to a transcatheter prosthetic valve replacement system.

BACKGROUND

The mitral valve refers to the entire structure composed of the mitral annulus, the anterior leaflet, the posterior leaflet, the chordae tendineae, the papillary muscles, the left atrium, and the left ventricle, in which the anterior leaflet and the posterior leaflet are separated by commissures therebetween which are respectively located anterolaterally and posteromedially. The chordae tendineae originating from the bilateral papillary muscles are inserted into the leaflets, and generally divided into the following three kinds according to the portions where they are inserted: the commissure chordae, the anterior leaflet chordae, and the posterior leaflet chordae. As the name suggests, the commissure chordae are inserted into the valve commissure and are normally fan-shaped chordae individually originated and branched from a papillary muscle, and inserted into the leaflet commissure. The anterior leaflet chordae are inserted into the free edge of the anterior leaflet to provide necessary support for the anterior leaflet of the valve. The posterior leaflet chordae are inserted into both the free edge and the base of the posterior leaflet.

The diseases of the mitral valve are the most common valve diseases and are mainly caused by the pathologic alteration of the valve itself or the secondary alteration induced by the left heart system diseases. As compared to the conventional invasive surgery such as the thoracotomy, the open heart surgery, and the extracorporeal circulation, the transcatheter interventional replacement surgery is becoming the first choice due to its numerous advantages such as decreased operating difficulty, shortened recovery time for the patient, and reduced pain of the patient. However, currently there is still no perfect solution regarding how to position and fasten the replacement device at the heart and how to adapt the replacement device for different physiological structures of the valve annuluses.

The patent CN103079498A describes a transcatheter mitral valve prosthesis including an anchor having an atrial skirt, an annular region, and a ventricular skirt. The ventricular skirt further includes a trigonal anchoring tab disposed on an anterior portion of the ventricular skirt. The trigonal anchoring tab is adapted to being anchored against a first fibrous trigon on a first side of an anterior leaflet of the patient's mitral valve, so that the anterior leaflet and adjacent chordae tendineae are captured between the trigonal anchoring tab and an anterior surface of the anchor. The ventricular skirt further includes a second trigonal anchoring tab disposed on the anterior portion of the ventricular skirt. The second trigonal anchoring tab is adapted to being anchored against a second fibrous trigon opposite the first fibrous trigon, so that the anterior leaflet and adjacent chordae tendineae are captured between the second trigonal anchoring tab and the anterior surface of the anchor. The ventricular skirt further includes a posterior ventricular anchoring tab disposed on a posterior portion of the ventricular skirt, and the posterior ventricular anchoring tab is adapted to being anchored over a posterior leaflet of the patient's mitral valve, so that the posterior ventricular anchoring tab is seated between the posterior leaflet and a ventricular wall of the patient's heart. According to the releasing manner in the patent, the ventricular skirt is radially expanded to displace the native mitral valve leaflets radially outward. At the same time as the radial expanding, the valve leaflets and the adjacent chordae tendineae are captured. The problem of this design is as follows. The releasing of the anchoring tab is irreversible, and it is difficult to ensure that the valve leaflets and the chordae tendineae thereof can be clamped in the one-time releasing. Before the releasing of the anchoring tab, the native valve leaflets have been partially opened and pressed by the annular region, and then a valve leaflet disabled period, during which the native valve leaflets have been disabled while the prosthetic valve leaflets have not started to work, occurs, thus affecting the normal blood-supply function of the heart of the patient. Being limited by the releasing position, the releasing configuration, and the condition of the chordae tendineae, the anchoring tab can only perform the covering and clamping action from the region of the valve leaflets barely having chordae tendineae. Whereas for the region of the valve leaflets having the chordae tendineae, the anchoring tab will be blocked by the chordae tendineae region, thereby causing an unsatisfactory clamping stability thereof.

In addition, Edwards Lifesciences Corporation of the United States disclosed a mitral valve replacement frame in U.S. Pat. No. 8,449,599. At least one clamping body is included at the outer surface of the frame. When the frame is compressed in the sheath, the gap between the clamping body and the outer surface of the frame is used to capture the valve leaflet. As the frame is gradually released, the gap between the clamping body and the outer surface of the frame gradually decreases to capture the valve leaflet therebetween. This design has the following problems. First, the frame and the clamping body are cut as one piece. The clamping ability of the clamping body is greatly affected by the wall thickness of the tubular material. The wall thickness of the tubular material in turn affects the supporting force of the frame. If the supporting force of the frame is too large, the tissue around the mitral valve such as the aortic valve will be pressed and the normal work thereof will be affected. Therefore, it is difficult for the designer to balance the supporting force of the frame and the pursuit of the relatively large clamping force of the clamping body. Second, the bending and shaping process of the clamping body is complex. Even the shaping is successful, the fatigue resistance of the clamping body is still controversial. Third, the clamping body can only perform the covering and clamping action from the region of the valve leaflet barely having the chordae tendineae, thereby causing an unsatisfactory clamping stability thereof. Fourth, the same clamping body can capture only one leaflet, and the regurgitation between the leaflets cannot be prevented.

In view of the above, although all of the above-described technologies have some effects on the valve repair, for the design of the anchoring mechanism of the existing product, there is a need to provide a valve prosthesis which can be accurately positioned and especially take full advantage of the chordae tendineae around the autologous valve leaflets to achieve more secure anchoring.

SUMMARY

The present application provides a transcatheter prosthetic valve replacement system, which not only achieves the clamping and fixing surrounding the frame, increases the area of the clamping and fixing, and improves the reliability of the fixing, but also, by compressing and releasing the clamping member, solves the problem that the clamping member is blocked and intervened by the autologous valve leaflet chordae tendineae, and significantly increases the success rate of the treatment.

A transcatheter prosthetic valve replacement system includes a delivery catheter, a frame, a prosthetic valve, and one or more clamping devices. The prosthetic valve is fixed in the frame. The clamping device is connected to a periphery of the frame. The frame and the clamping device can be preloaded in the delivery catheter. The clamping device includes a clamping member, a collar, and a control member. One end of the clamping member is a fixation end which is fixedly connected to the frame, and the other end of the clamping member is a deployable resilient segment which can be compressed and released. The collar is slidably sleeved on the clamping member. One end of the control member is connected to the collar, and the other end of the control member is configured to be manipulated outside the patient's body. From being compressed to being fully released, the clamping member in sequence has two configurations. In the first configuration, the collar is moved along the clamping member towards a free end of the deployable resilient segment, and the deployable resilient segment is gradually closed. In the second configuration, the collar is moved along the deployable resilient segment towards the fixation end, and the deployable resilient segment recovers its predetermined shape.

In an embodiment, the deployable resilient segment includes a collar-limiting unit. The collar-limiting unit is a protruding structure.

In an embodiment, the collar-limiting unit is located at a distal end portion or a proximal end portion of the deployable resilient segment, or the distal end portion and the proximal end portion of the deployable resilient segment are both disposed with the collar-limiting unit. When the clamping member is in the first configuration, and the deployable resilient segment is closed, the position of the collar is limited by the collar-limiting unit.

In an embodiment, the collar has an inner hole having a diameter-varying structure. In an embodiment, the inner hole of the collar has a tapered structure.

In an embodiment, the predetermined shape of the deployable resilient segment is shape of circumferentially surrounding the frame.

In an embodiment, a connecting portion between the clamping member and the frame is pre-shaped to a bending structure.

In an embodiment, the clamping member placed in the delivery catheter in a reflexed form. The free end of the clamping member is located at a side of a proximal end of the frame. From being compressed to being fully released, the clamping member in sequence has two configurations. In the first configuration, the collar is drawn by the control member to move along the clamping member towards the free end of the deployable resilient segment, and the deployable resilient segment is gradually closed. In the second configuration, after the connecting portion between the clamping member and the frame recovers the bending structure, the collar is continued to be drawn by the control member to move along the deployable resilient segment towards the fixation end, and the deployable resilient segment recovers the predetermined shape.

In an embodiment, the clamping member is a Y-shaped or T-shaped structure.

In an embodiment, a flexible buffer device is disposed at an end of the deployable resilient segment.

In an embodiment, that the clamping structure is in one piece, or the clamping member and the frame are made in one piece from a memory alloy.

In an embodiment, the one end of the control member is detachably connected to the collar.

In an embodiment, the transcatheter prosthetic valve replacement system further includes a handle. The other end of the control member is detachably connected to the handle.

In an embodiment, the frame comprises a valve frame and a self-adaption frame. The self-adaption frame is fixedly connected to a periphery of the valve frame. The clamping member is fixed to the self-adaption frame.

In an embodiment, the control member is a drawstring or a rod.

As compared to the prior art, the present application has the following advantages.

1. In the present application, the design of the structure of the deployable resilient segment allows the clamping member to access the specified working position without being blocked. During the access, the clamping member is prevented from being in contact with the autologous tissues, thereby reducing the damage to the body tissues. Moreover, the clamping area is increased and the clamping effect is enhanced after the deployable resilient segment is fully released.

2. In the present application, the collar-limiting unit is disposed on the deployable resilient segment. This design can prevent the misoperation and the loosing of the collar, which will cause the deployable resilient segment to early recover its predetermined shape, in the loading and releasing processes, thereby increasing the reliably and security of the apparatus.

3. In the present application, the clamping member is placed in the delivery catheter in the reflexed form. On the one hand, the overlap with the frame can be avoided, significantly reducing the sheath size. On the other hand, the directions of the force arms of the control member during recovering the bending structure and gradually releasing the clamping member is ably utilized to enable the deployable resilient segment to arrive, in the closed state, the back of the autologous valve leaflets and then automatically recover the shape circumferentially surrounding the frame.

4. In the present application, the flexible buffer device is disposed at the end of the deployable resilient segment for the purpose of preventing the damage to the autologous valve annulus and the tissues around the autologous valve annulus.

BRIEF DESCRIPTION OF THE DRAWINGS

FIG. 1A to FIG. 1D are schematic views showing the delivery and the clamping of an existing product.

FIG. 2A to FIG. 2C are schematic views showing an embodiment of a transcatheter prosthetic valve replacement system of the present application.

FIG. 3A and FIG. 3B are schematic views showing an embodiment of a collar of the present application.

FIG. 4A to FIG. 4I are schematic views showing steps of a releasing manner of the present application, in which FIG. 4H is an enlarged partial view of FIG. 4G.

DETAILED DESCRIPTION

Figure 4C:
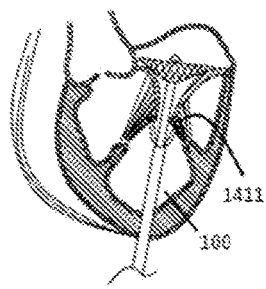

In order to make the objects, technical schemes, and advantages of the present application more clear and understandable, the present application will be described in more details with reference to the accompanying figures and embodiments.

The distal end described in the present application refers to the end farther from the apex of the heart, and the proximal end described in the present application refers to the end nearer to the apex of the heart.

Example 1

Referring to FIG. 1A which shows the left ventricle 016 and the left atrium 017 of the left half of the heart, the blood can flow unidirectionally from the left atrium 017 into the left ventricle 016. The mitral valve of the heart is located at the communicating area between the left atrium 017 and the left ventricle 016, and includes the mitral annulus 011, the anterior leaflet 012, the posterior leaflet 013, the chordae tendineae 014, and the papillary muscles 015. The anterior leaflet 012 and the posterior leaflet 013 are respectively connected to the corresponding papillary muscles 015 via their own chordae tendineae 014. In a healthy heart organ, when the papillary muscles 015 contract to tense the chordae tendineae 014, the mitral valve is in an open state; and when the papillary muscles 015 relax to loose the chordae tendineae 014, the mitral valve is in a closed state.

Referring to FIG. 1B, the mitral valve is generally divided by the person skilled in the art into several regions, in which the anterior leaflet 012 (A1, A2, A3) and the posterior leaflet 013 (P1, P2, P3) are separated by commissures therebetween which are respectively located anterolaterally and posteromedially. The chordae tendineae are mainly distributed at the commissures between the anterior leaflet 012 and the posterior leaflet 013. Normally, the convex portions of the anterior leaflet 012 and the posterior leaflet 013 have no chordae tendineae bound thereto, and thus are the main areas of the mitral valve to connect the artificial valve prosthesis.

Referring to FIG. 1C and FIG. 1D, all of the existing products, such as Edwards's TIARA and Neovasc's FORTIS, adopt anchoring tab structures 018 fixed on a frame and approaching the valve annulus from the free portions of the valve leaflets. Furthermore, referring to FIG. 1D, the anchoring tabs 108, both during inserting to the back of the valve leaflets and at the final clamping positions, substantially bypass the chordae tendineae (the anchoring tab structures 018 are generally located at the region A2 and the region P2). As the clamping area is limited, the nearby chordae tendineae structures are underutilized, and the anchoring is not secure and reliable enough.

Referring to FIG. 2A to FIG. 2C, a transcatheter prosthetic valve replacement system 100 according to the present application includes a delivery catheter 110, a frame 120, a prosthetic valve 130, two clamping devices 140, and a handle 150. The prosthetic valve 130 is fixed in the frame 120. The clamping devices 140 are connected to a periphery of the frame 120. The frame 120 and the clamping devices 140 can be preloaded in the delivery catheter 110. The clamping device 140 includes a clamping member 141, a collar 142, and a control member 143. The control member 143 is a drawstring. One end of the clamping member 141 is a fixation end 1410 which is fixedly connected to the frame 120. The other end of the clamping member 141 is free and is a deployable resilient segment 1411 which can be compressed and released. The collar 142 is slidably sleeved on the clamping member 141. One end of the control member 143 is connected to the collar 142, and the other end of the control member 143 is connected to the handle 150 in order to be manipulated outside the body. From being compressed to being fully released, the clamping member 141 in sequence has two configurations. In the first configuration, the collar 142 is moved along the clamping member 141 towards the free end of the deployable resilient segment 1411, so that the deployable resilient segment 1411 is gradually closed (FIG. 2B). In the second configuration, the collar 142 is moved along the deployable resilient segment 1411 towards the fixation end 1410, so that the deployable resilient segment 1411 recovers its predetermined shape. The predetermined shape of the deployable resilient segment 1411 is a shape circumferentially surrounding the frame 120 (FIG. 2C). The structure designs of the fixation end 1410 and the deployable resilient segment 1411 of the clamping member 141 allow the clamping member 141 to access the specified working position without being blocked. During the access, the clamping member 141 is prevented from being in contact with the autologous tissues, thereby reducing the damage to the body tissues. Moreover, the clamping area is increased and the clamping effect is enhanced after the deployable resilient segment 1411 is fully released. The clamping member 141 is a Y-shaped or T-shaped structure made in one piece from a memory alloy. The clamping member 141 and the frame 120 are made in one piece from a memory alloy.

As an embodiment, referring to FIG. 3A and FIG. 3B, the inner hole of the collar 142 is a diameter-varying structure. The deployable resilient segment 1411 includes a collar-limiting unit 1421. The collar-limiting unit 1421 is a protruding structure. The collar-limiting unit 1421 is located at a proximal end portion of the deployable resilient segment 1411. When the clamping member 141 is in the first configuration, and the deployable resilient segment 1411 is closed, the position of the collar 142 is limited by the collar-limiting unit 1421. This design can prevent the misoperation of the collar 142, which will cause the deployable resilient segment 1411 to early recover its predetermined shape, in the loading and releasing processes, thus improving the reliability and the security of the apparatus. The control member 143 can be detachably connected to the collar 142.

To better illustrate the present embodiment, the operation steps of the transcatheter prosthetic valve replacement system 100 is described as follows.

(1) Referring to FIG. 4A and FIG. 4B, the implant including the frame 120, the prosthetic valve 130, and two clamping devices 140 is compressed and loaded into the delivery catheter 110. With the assistance of an imaging instrument, the implant is delivered to the lesion site of the patient via a heart apex approach path. At this time, the clamping members 141 are in the first configuration; that is, the collars 142 are moved along the clamping members 141 towards the free ends of the deployable resilient segments 1411 until the positions of the collars 142 are limited by the collar-limiting units (not shown in the figures), and the deployable resilient segments 1411 are fully closed.

Figure 4D:
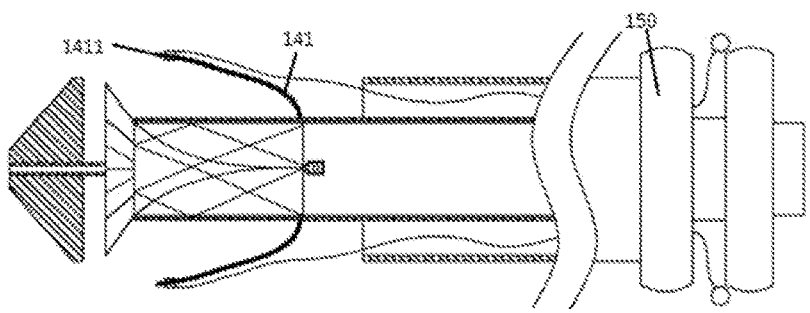

(2) Referring to FIG. 4C and FIG. 4D, the handle 150 is manipulated such that the deployable resilient segments 1411 are partially released. With the assistance of the imaging instrument, the replacement system 100 is adjusted such that the free ends of the deployable resilient segments 1411 pass through the chordae tendineae and are opened with an opening angle in a direction away from the central axis of the autologous mitral valve.

Figure 4E:
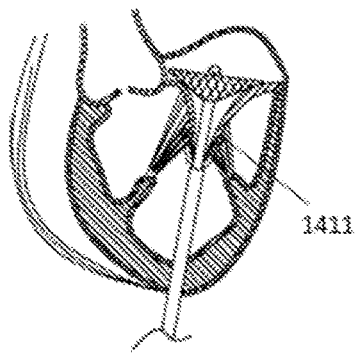

(3) Referring to FIG. 4E, the whole replacement system 100 is moved such that the free ends of the deployable resilient segments 1411 are moved to the roots of the autologous valve leaflets of the patient, causing the free ends of the deployable resilient segments 1411 to be located opposite to a closure face of the autologous valve leaflets. The closure face of the autologous valve leaflets refers to the face where the closed area of the autologous valve leaflets is located when the valve leaflets are closed.

Figure 4F:
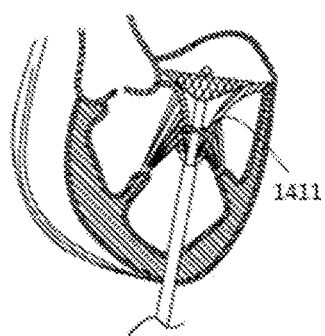
Figure 4G:
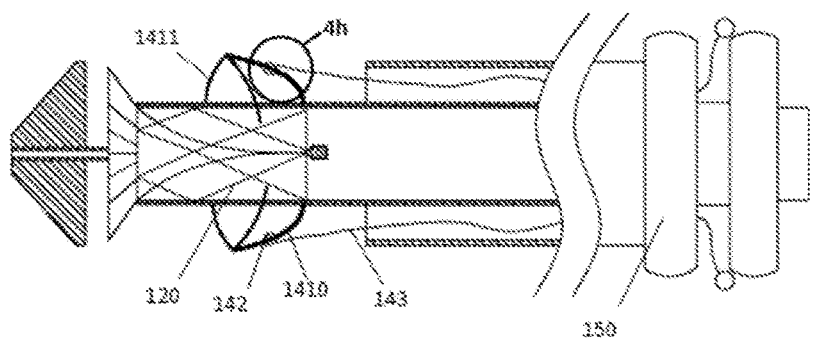

(4) Referring to FIG. 4F and FIG. 4G, the handle 150 is further manipulated to draw the control members 143 to move the collars 142 along the clamping members 141 to the fixation ends 1410, so that the deployable resilient segments 1411 recover the shape circumferentially surrounding the frame 120. At this time, the clamping members 141 are in the second configuration; that is, the fully released deployable resilient segments 1411 are located opposite to the closure face of the autologous valve leaflets and recover the predetermined shape.

Figure 4H:
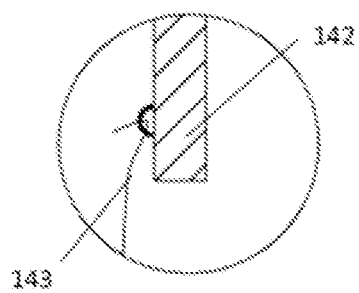

(5) Referring to FIG. 4H, the control members 143 and the collars 142 are detached to separate the control members 143 from the collars 142; that is, the control members 143 and the collars 142 are detachably connected to each other.

Figure 4I:
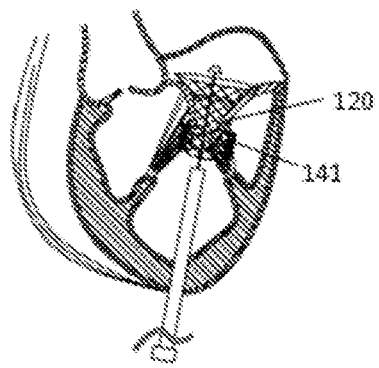

(6) Referring to FIG. 4I, the handle is manipulated such that the frame 120 is fully released, causing the autologous valve leaflets to be clamped between the clamping members 141 and the outer surface of the frame 120.

(7) The delivery catheter 110 is manipulated to be withdrawn from the human body.

Example 2

Figure 5A:
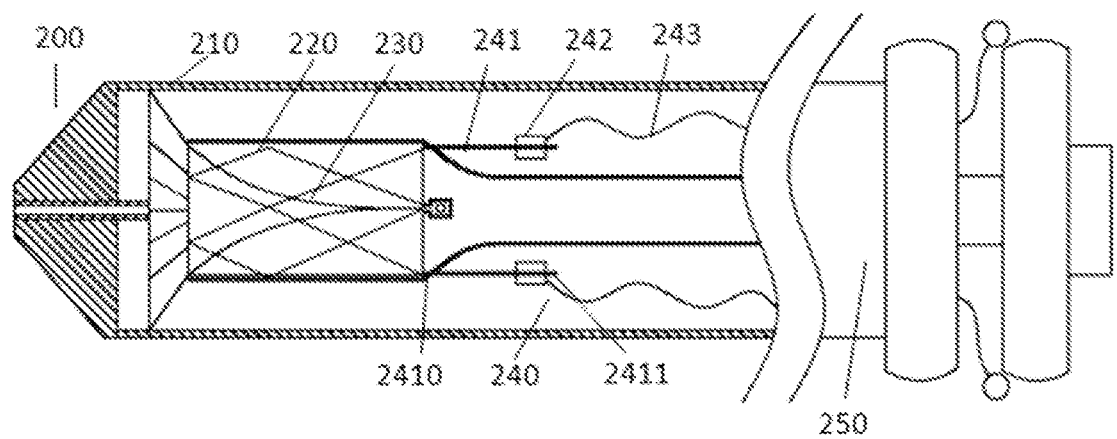
FIG. 5A to FIG. 5C are schematic views showing another embodiment of the transcatheter prosthetic valve replacement system of the present application.
Figure 5B:
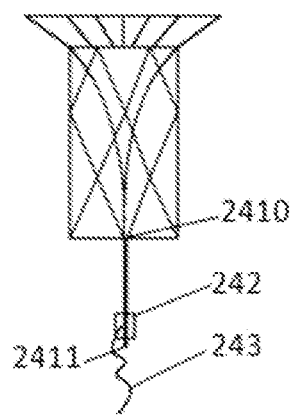
Figure 5C:
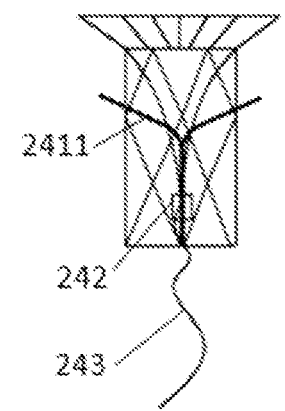

Referring to FIG. 5A to FIG. 5C, as another embodiment, a transcatheter prosthetic valve replacement system 200 includes a delivery catheter 210, a frame 220, a prosthetic valve 230, two clamping devices 240, and a handle 250. The prosthetic valve 230 is fixed in the frame 220. The clamping devices 240 are connected to a periphery of the frame 220. The frame 220 and the clamping devices 240 can be preloaded in the delivery catheter 210. The clamping device 240 includes a clamping member 241, a collar 242, and a control member 243. One end of the clamping member 241 is a fixation end 2410 which is fixedly connected to the frame 220. The other end of the clamping member 241 is a deployable resilient segment 2411 which can be compressed and released. The deployable resilient segment 2411 is pre-shaped in a shape circumferentially surrounding the frame. The collar 242 is slidably sleeved on the clamping member 241. One end of the control member 243 is connected to the collar 242, and the other end of the control member 243 is connected to the handle 250. From being compressed to being fully released, the clamping member 241 in sequence has two configurations. In the first configuration, the collar 242 is moved along the clamping member 241 towards the free end of the deployable resilient segment 2411, so that the deployable resilient segment 2411 is gradually closed. In the second configuration, the collar 242 is moved along the deployable resilient segment 2411 towards the fixation end 2410, so that the deployable resilient segment 2411 recovers its shape circumferentially surrounding the frame 220. The control member 243 is detachably connected to the handle 250.

Figure 6A:
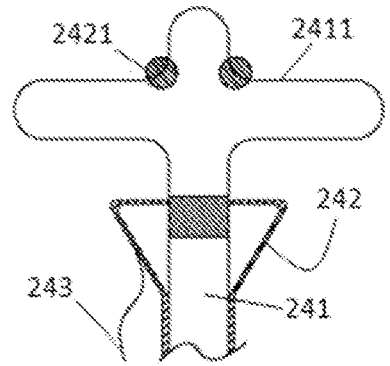
FIG. 6A to FIG. 6D are schematic views showing various embodiments of a clamping device of the present application.
Figure 6B:
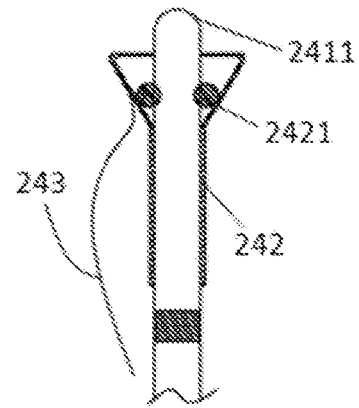
Figure 6C:
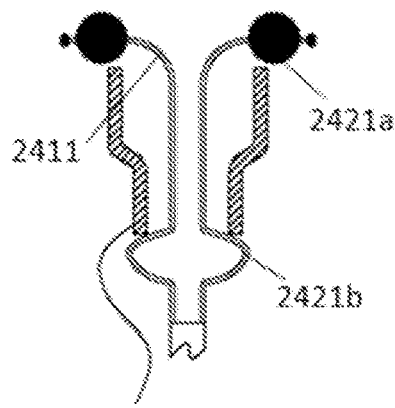
Figure 6D:
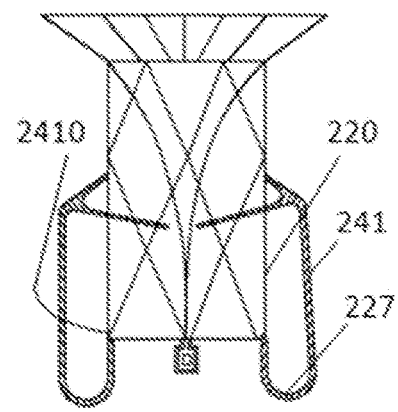

As an embodiment, referring to FIG. 6A and FIG. 6B, the deployable resilient segment 2411 is connected to the remaining portion of the clamping member 241 via an annular tube. The inner hole of the collar 242 has a tapered structure. The deployable resilient segment 2411 includes a collar-limiting unit 2421. The collar-limiting unit 2421 is a protruding structure. The collar-limiting unit 2421 is located at a distal end portion of the deployable resilient segment 2411. When the clamping member 241 is in the first configuration, and the deployable resilient segment 2411 is closed, the position of the collar 242 is limited by the collar-limiting unit 2421. This design is advantaged in that it can prevent the loosing of the collar 142 in the loading and releasing processes, which will cause the deployable resilient segment 2411 to early recover its predetermined shape, thereby improving the reliability and the security of the apparatus. Referring to FIG. 6C, the collar-limiting units 2421 (2421a, 2421b) are disposed at both the distal end portion and the proximal end portion of the deployable resilient segment 2411, which can maximally ensure the reliability of the apparatus. A flexible buffer device is disposed at the end of the deployable resilient segment 2411 for the purpose of preventing the damage to the autologous valve annulus and the tissues around the autologous valve annulus. Referring to FIG. 6D, the clamping member 241 and the frame 220 are made in one piece from a memory alloy. In the natural state, a connecting portion 227 between the clamping member 241 and the frame 220 is pre-shaped to a bending structure.

To better illustrate the present embodiment, the operation steps of the transcatheter prosthetic valve replacement system is described as follows.

Figure 7A:
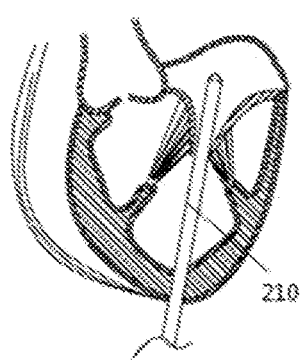
FIG. 7A to FIG. 7J are schematic views showing steps of another releasing manner of the present application.
Figure 7B:
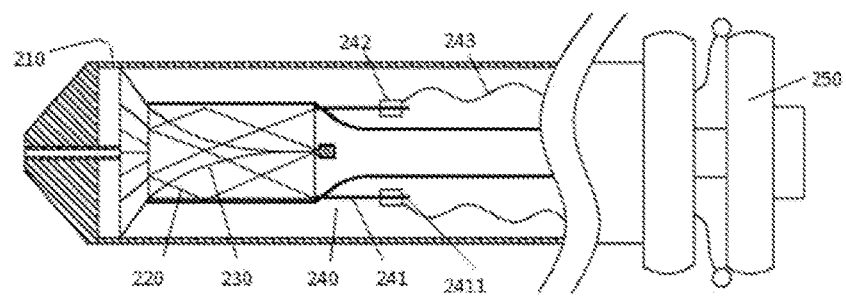

(1) Referring to FIG. 7A and FIG. 7B, the implant including the frame 220, the prosthetic valve 230, and the two clamping devices 440 is compressed and loaded into the delivery catheter 210. At this time, the clamping members 241 are placed in the delivery catheter 210 in a reflexed form, and the free ends of the deployable resilient segments 2411 are located at the side of the proximal end of the frame 220. With the assistance of the imaging instrument, the implant is delivered to the lesion site of the patient via a heart apex approach path. At this time, the clamping members 241 are in the first configuration; that is, the control members 243 draw the collars 242 to move the collars 242 along the clamping members 241 towards the free ends of the deployable resilient segments 2411 until the positions of the collars 242 are limited by the collar-limiting units (not shown in the figures), and the deployable resilient segments 2411 are fully closed.

Figure 7C:
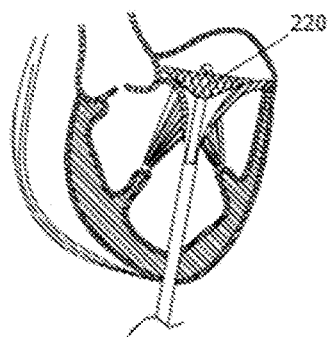

(2) Referring to FIG. 7C, the handle 250 is manipulated such that the distal end of the frame 220 is released, and the distal end of the frame 220 is adjusted to abut against the mitral annulus.

Figures 7D, 7E:
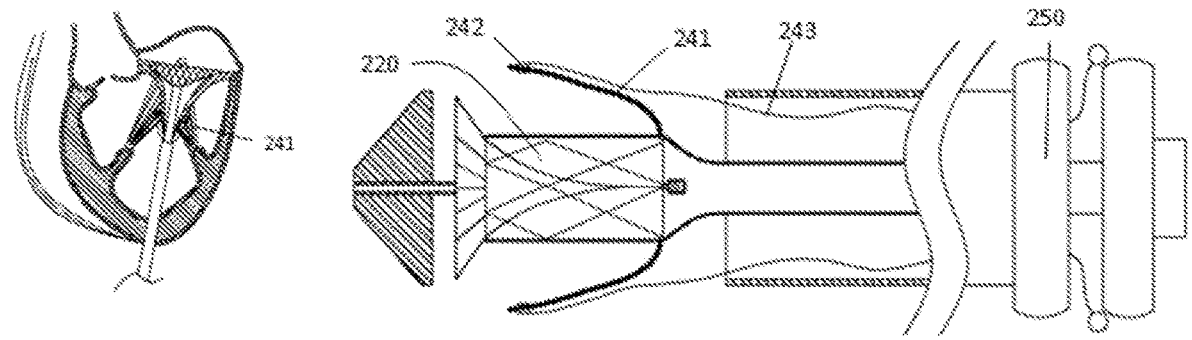
Figure 7F:
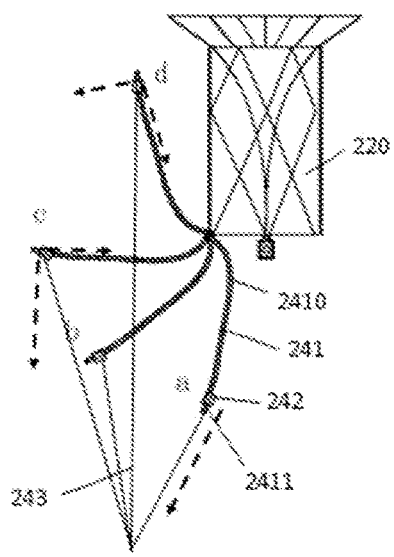

(3) Referring to FIG. 7D to 7F, the handle 250 is manipulated such that the free portions of the clamping members 241 are gradually released, and the connecting portions between the clamping members 241 and the frame 220 recover their bending structure. Referring to FIG. 7F, the clamping members 241 in sequence arrive positions a, b, c, and d. In the phase from a to b to c, since the directions of the forces subjected by the collar 242 are always pointed to the control member 243, it can be seen from the decomposition of the forces (dotted lines) that the collar 242 has no tendency to move along the clamping member 241 towards the fixation end 2410. With the assist of the imaging instrument, the replacement system 200 is adjusted such that the free ends of the deployable resilient segments 2411 pass through the chordae tendineae. In the phase from c to d, since the directions of the forces subjected by the collar 242 are always pointed to the control member 243, it can be seen from the decomposition of the forces that if the control member 243 is continued to be drawn, the collar 242 tends to be moved along the clamping member 241 towards the fixation end 2410.

(4) The whole replacement system 200 is moved such that the free ends of the deployable resilient segments 2411 are moved to the roots of the autologous valve leaflets of the patient, causing the free ends of the deployable resilient segments 2411 to be located opposite to a closure face of the autologous valve leaflets. The closure face of the autologous valve leaflets refers to the face where the closed area of the autologous valve leaflets is located when the valve leaflets are closed.

Figure 7G:
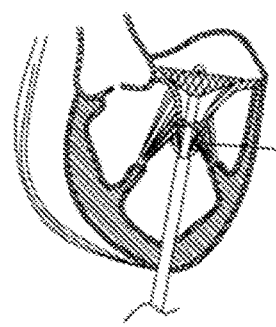
Figure 7H:
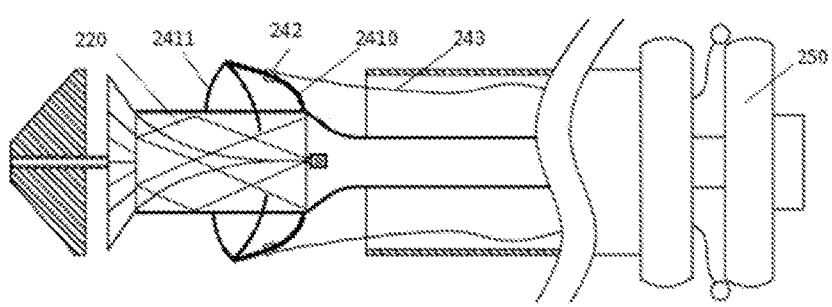

(5) Referring to FIG. 7G and FIG. 7H, the handle 250 is further manipulated to draw the control members 243 to move the collars 242 along the deployable resilient segments 2411 to the fixation ends 2410, so that the deployable resilient segments 2411 recover the shape circumferentially surrounding the frame 220. At this time, the clamping member 242 is in the second configuration; that is, the fully released deployable resilient segments 2411 are located opposite to the closure face of the autologous valve leaflets and recover the predetermined shape.

Figure 7I:
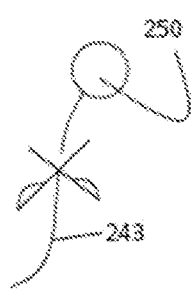

(6) Referring to FIG. 7I, the control members 243 and the handle 250 are detached to separate the control members 243 from the handle 250.

Figure 7J:
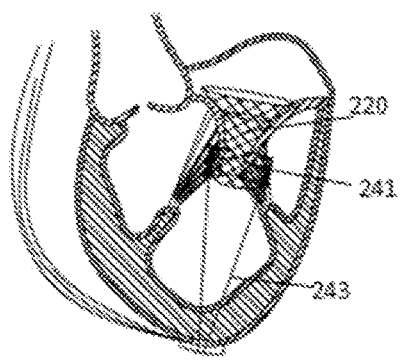

(7) Referring to FIG. 7J, the handle 250 is manipulated such that the frame 220 is fully released, causing the autologous valve leaflets to be clamped between the clamping members 241 and the outer surface of the frame 220. The delivery catheter 210 is manipulated to be withdrawn from the human body. The control members 243 are stitched to the apex of the heart.

In the present embodiment, the clamping members 241 are placed in the delivery catheter 210 in the reflexed form. On the one hand, the overlap with the frame is avoided, thereby significantly reducing the sheath size, and on the other hand, the directions of the forces subjected by the control member 243 during recovering the bending structure and gradually releasing the clamping member 241 are ably utilized to allow the deployable resilient segments 2411 to arrive, in the closed state, the back of the autologous valve leaflets and then automatically recover the shape circumferentially surrounding the frame 120.

Figure 8:
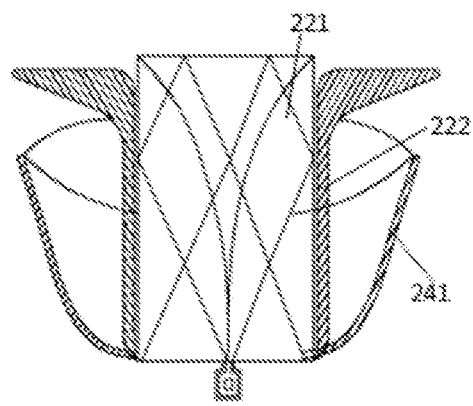
FIG. 8 is a schematic view showing another embodiment of the present application.

As another embodiment, referring to FIG. 8, the frame 220 includes a valve frame 221 and a self-adaption frame 222. The self-adaption frame 222 is fixedly connected to a periphery of the valve frame 221. The clamping members 241 are fixed to the self-adaption frame 222. The self-adaption frame 222 has a flexible structure which can follow the profile and movement of the valve annulus, so as to ensure that the valve frame 221 will not be deformed with the deformation of the self-adaption frame 222.

Figure 9:
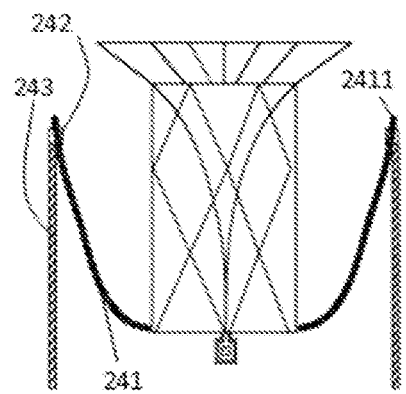
FIG. 9 is a schematic view showing an embodiment of a control member of the present application.

As another embodiment, referring to FIG. 9, the control members 243 are rods and have a certain rigidity, so that they can control the collars 242 to slide up and down along the clamping members 241 to repeatedly retract and release the deployable resilient segments 2411. This design has the following advantages: The positioning and the releasing can be repeatedly performed by the surgeon in operation, thereby increasing the surgical safety.

In addition to the mitral valve, the technical schemes of the present application can also be applied to treat the patients with the diseases of the tricuspid valve, the aortic valve, and the pulmonary valve.

The technical features of the above-described embodiments may be arbitrarily combined. In order to make the description simple, not all possible combinations of the technical features in the above embodiments are described. However, as long as there is no contradiction in the combination of these technical features, the combinations should be in the scope of the present application.

What described above are only several embodiments of the present application, and these embodiments are specific and detailed, but not intended to limit the scope of the present application. It should be understood by one ordinary skill in the art that various modifications and improvements can be made without departing from the conception of the present application, and all fall within the protection scope of the present application. Therefore, the patent protection scope of the present application is defined by the appended claims.

What is claimed is:

1. A transcatheter prosthetic valve replacement system, comprising;

a delivery catheter, a frame, a prosthetic valve, and one or more clamping devices, wherein the prosthetic valve is fixed in the frame, the clamping device is connected to a periphery of the frame, and the frame and the clamping device are capable of being preloaded in the delivery catheter; the clamping device comprises a clamping member, a collar configured to surround the clamping member, and a control member; one end of the clamping member is a fixation end which is fixedly connected to the frame, the other end of the clamping member is a deployable resilient segment which is capable of being compressed and released; the collar is slidably sleeved on the clamping member; one end of the control member is connected to the collar, and the other end of the control member is configured to be manipulated outside the patient's body; from being compressed to being fully released, the clamping member in sequence has two configurations, in the first configuration, the collar is moved along the clamping member towards a free end of the deployable resilient segment and the deployable resilient segment is gradually closed, and in the second configuration, the collar is moved along the deployable resilient segment towards the fixation end and the deployable resilient segment recovers its predetermined shape.

2. The transcatheter prosthetic valve replacement system of claim 1, wherein the deployable resilient segment comprises a collar-limiting unit, and the collar-limiting unit is a protruding structure.

3. The transcatheter prosthetic valve replacement system of claim 2, wherein when the clamping member is in the first configuration, and the deployable resilient segment is closed, the position of the collar is limited by the collar-limiting unit.

4. The transcatheter prosthetic valve replacement system of claim 1, wherein the collar has an inner hole having a diameter-varying structure.

5. The transcatheter prosthetic valve replacement system of claim 4, wherein the diameter-varying structure is a tapered structure.

6. The transcatheter prosthetic valve replacement system of claim 1, wherein the predetermined shape of the deployable resilient segment is a shape circumferentially surrounding the frame.

7. The transcatheter prosthetic valve replacement system of claim 1, wherein a connecting portion between the clamping member and the frame is pre-shaped to a bending structure.

8. The transcatheter prosthetic valve replacement system of claim 7, wherein the clamping member is placed in the delivery catheter in a reflexed form, the free end of the clamping member is located at a side of a proximal end of the frame; from being compressed to being fully released, the clamping member in sequence has two configurations, in the first configuration, the collar is drawn by the control member to move along the clamping member towards the free end of the deployable resilient segment, and the deployable resilient segment is gradually closed, and in the second configuration, after the connecting portion between the clamping member and the frame recovers the bending structure, the collar is continued to be drawn by the control member to move along the deployable resilient segment towards the fixation end, and the deployable resilient segment recovers the predetermined shape.

9. The transcatheter prosthetic valve replacement system of claim 1, wherein the clamping member is a Y-shaped or T-shaped structure.

10. The transcatheter prosthetic valve replacement system of claim 1, wherein a flexible buffer device is disposed at an end of the deployable resilient segment.

11. The transcatheter prosthetic valve replacement system of claim 1, wherein the clamping structure is in one piece, or the clamping member and the frame are made in one piece from a memory alloy.

12. The transcatheter prosthetic valve replacement system of claim 1, wherein the end of the control member is detachably connected to the collar.

13. The transcatheter prosthetic valve replacement system of claim 12, further comprising a handle detachably connected to the other end of the control member.

14. The transcatheter prosthetic valve replacement system of claim 1, wherein the frame comprises a valve frame and a self-adaption frame, the self-adaption frame is fixedly connected to a periphery of the valve frame, and the clamping member is fixed to the self-adaption frame.

15. The transcatheter prosthetic valve replacement system of claim 1, wherein the control member is a drawstring or a rod.

* * * * *